(12) United States Patent
Mirkov et al.

(10) Patent No.: US 7,323,622 B2
(45) Date of Patent: Jan. 29, 2008

(54) STEM-REGULATED, PLANT DEFENSE PROMOTER AND USES THEREOF IN TISSUE-SPECIFIC EXPRESSION IN MONOCOTS

(75) Inventors: T. Erik Mirkov, Harlingen, TX (US); Mona B. Damaj, College Station, TX (US); Avutu Reddy, Carmel, IN (US); Terry L. Thomas, College Station, TX (US); Keerti S. Rathore, College Station, TX (US); Chandrakanth Emani, College Station, TX (US); Siva Prasad Kumpatla, Zionsville, IN (US)

(73) Assignee: The Texas A&M University System, College Station, TX (US)

( * ) Notice: Subject to any disclaimer, the term of this patent is extended or adjusted under 35 U.S.C. 154(b) by 12 days.

(21) Appl. No.: 10/751,612

(22) Filed: Jan. 5, 2004

(65) Prior Publication Data

US 2005/0005322 A1    Jan. 6, 2005

Related U.S. Application Data

(60) Provisional application No. 60/437,890, filed on Jan. 3, 2003.

(51) Int. Cl.
*A01H 5/00*   (2006.01)
*C12N 15/82*   (2006.01)
*C07H 21/04*   (2006.01)

(52) U.S. Cl. .................. 800/287; 800/320; 800/302; 435/320.1; 435/468; 435/471; 435/419; 435/252.3; 536/24.1

(58) Field of Classification Search ................ 800/278, 800/287, 293, 294, 298; 536/24.1; 435/320.1, 435/419, 468, 471, 252, 3
See application file for complete search history.

(56) References Cited

U.S. PATENT DOCUMENTS

| 5,510,474 A | 4/1996 | Quail et al. ................. 536/24.1 |
| 5,641,876 A | 6/1997 | McElroy et al. ............. 536/24.1 |
| 5,712,112 A | 1/1998 | Yu et al. ..................... 435/69.1 |
| 6,359,196 B1 | 3/2002 | Lok et al. ................... 800/278 |

OTHER PUBLICATIONS

Ulmasov et al., *Composite Structure of Auxin Response Elements*, The Plant Cell 7:1611-1623, 1995.*
Donald et al., *Mutation of either G box or I box sequences profoundly affects expression from the Arabidopsis rbcS-1A promoter*, The EMBO Journal 9: 1717-1726, 1990.*
Aldemita et al., *Agrobacterium Tumefaciens-Mediated Transformation of Japonica and Indica Rice Varieties*, Planta, vol. 199, pp. 612-617, 1996.
Altschul, et al., *Gapped BLAST and PSI-BLAST: a new generation of protein database search programs*, Nucleac Acids Research, vol. 25, No. 17, pp. 3389-3942, 1997.
Barton, et al., *Regeneration of Intact Tobacco Plants Containing Full Length Copies of Genetically Engineered T-DNA, and Transmission of T-DNA to R1 Progeny*, Cell, vol. 32, 1033-1043, 1983.
Chen, et al., *Laboratory Methods Supercoil Sequencing: A Fast and Simple Method for Sequencing Plasmid DNA*, DNA, vol. 4, No. 2, pp. 165-170, 1985.
Damaj, et al., *Functional Genomics in Sugarcane: Macro- and Microarray Analyses to Determine the Tissue-specific Expression of Candidate Genes*, Plant, Animal & Microbe Genome X Conference (abstract only), Jan. 2001.
Damaj, et al., *Isolation of Tisue Specific Promoters to Engineer Sugarcane for Improved Argonomic Traits*, Plant, Animal & Microbe Genome X Conference, (abstract only), Jan. 2001.
Hajdukiewicz, et al., *The small, versatile pPXP family of Agrobacterium binary vectors for plant transformation*, Plant Molecular Biology 25, pp. 989-994, 1994.
Held, et al., *An mRNA Putatively Coding for an O-Methyltransferase AccumulatesPreferentially in Maize Roots and Is Located Predominantly in the Region of the Endodermis*, Plant Physiol., 102, pp. 1001-1008, 1993.
Horsch, et al., *Inheritance of Functional Foreign Genes in Plants*, Science, vol. 223, pp. 496-498, 1984.
Horsch, et al., *A simple and General Method for Transferring Genes into Plants*, Scienc,e vol. 227, pp. 1229-1231, 1985.
Huang, et al., *The tissue-specific activity of a rice beta-glucanase promoter (Gns9) is used to select rice transformants*, Plant Science, 161, pp. 589-595, 2001.
Ingelbrecht, et. al., *Posttranscriptional Gene Silencing in Transgenic Sugarcane. Dissection of Homology-Dependent Virus Resistance in a Monocot That Has a Complex Polyploid Genome*,Plant Physiology, vol. 119, pp. 1187-1197, Apr. 1999.
Irvine, et al., *The Development Of Genetic Transformation Of Sugarcane in Texas*, Sugar Journal, pp. 25-29, Jun. 1997.
Ito, et al., *Xylem-specific expression of wound-inducible rice peroxidase genes in transgeneic plants*, Plant Science, 155, pp. 85-100, 2000.
Jach, et al., *Enhanced quantitative resistance against fungal disease by combinatorial expression of different barley antifungal proteins in transgenic tobacco*, The Plant Journal 8(1), 97-109, 1995.
Jefferson, et al., *GUS fusions: β-glucuronidase as a sensitive and versatile gene fusion marker in higher plants*, The EMBO Journal, vol. 6 No. 13, pp. 3901-3907, 1987.

(Continued)

*Primary Examiner*—Elizabeth F. McElwain
(74) *Attorney, Agent, or Firm*—Baker Botts L.L.P.

(57)    ABSTRACT

The invention is directed to isolated promoters from stem-regulated, defense-inducible genes, such as OMT promoters. The promoters are useful in expression cassettes and expression vectors for the transformation of plants. Particularly, the invention provides transgenic plants of rice and sugarcane that have been modified such that expression of a heterologous coding sequence is directed by an OMT promoter and is limited to stem tissues or may be upregulated by the presence of a defense-inducing agent. The invention also discloses methods for producing the expression vectors and transgenic plants.

32 Claims, 15 Drawing Sheets
(6 of 15 Drawing Sheet(s) Filed in Color)

OTHER PUBLICATIONS

Jensen, et al., *Transgenic barley expressing a protien-engineered, thermostable (1,3-1,4)-β-glucanase during germination,* Proc. Natl. Acad. Sci. USA, vol. 93, pp. 3487-3491, Apr. 1996.

Klein, et al., *High-velocity microprojectiles for delivering nucleic acids into living cells,* Nature, vol. 327, pp. 70-73, May 1987.

Mikkonen, et al., *A major cysteine proteinase, EPB, in germinating barley seeds: structure of two intronless genes and regulation of expression,* Plant Molecular Biology, 31, pp. 239-254, 1996.

Mitsuhara, et al., *Efficient Promoter Cassettes for Enhanced Expression of Foreign Genes in Dicotyledonous and Monocotyledonous Plants,* Plant Cell Physiol., 37(1), pp. 49-59, 1996.

Muhitch, et al., *Isolation of a promoter sequence from the glutanine synthetase$_{1-2}$ gene capable of conferring tisue-specific gene expression in transgenic maize,* Plant Science, 163, pp. 865-872, 2002.

Napoli, et al., *Introduction of a Chimeric Chalcone Synthase Gene into Petunia Results in Reversible Co-Suppression of Homologous Genes in trans,* The Plant Cell, vol. 2, pp. 279-289, Apr. 1990.

Pearson, et al., *Improved tools for biological sequence comparison,* Proc. Natl. Acad. Sci USA, vol. 85, pp. 2444-2448, Apr. 1988.

Pearson, [5] *Rapid and Sensitive Sequence Comparison with FASTP and FASTA,* Methods in Enzymology, vol. 183, pp. 63-98, 1990.

Schenk, et al., *Promoters for pregenomic RNA of banana streak badnavirus are active for transgene expression in monocot and dicot plants,* Plant Molecular Biology, 47, pp. 399-412, 2001.

van der Krol, et al., *Inhibition of flower pigmentation by antisense CHS genes: promoter and minimal sequence requirements for the antisense effect,* Plant Molecular Biology, 14, pp. 457-466, 1990.

Wei, et al., *Comparative expression analysis of two sugarcane polyubiquitin promoters and flanking sequences in transgenic plants,* J. Plant Physiol. 160, pp. 1241-1251, 2003.

Wei, et al., *Differential Expression of Sugarcane Polyubiquitin Genes and Isolation of Promoters from two Highly-Expressed Members of the Gene Family,* J. Plant Physiol. vol. 155, pp. 513-519, 1999.

Wolf, *Structure of the genes encoding Hordeum vulgare ($1 \rightarrow 3, 1 \rightarrow 4$)-β-glucanase isoenzymes I and II and functional analysis of their promoters in barley aleurone protoplasts,* Mol Gen Genete, 234, pp. 33-42, 1992.

Yin, et al., *Promoter elements required for pholoem-specific gene expression from the RTBV promoter in rice,* The Plant Journal, 12(5), pp. 1179-1188, 1997.

Zambryski, et al., *Ti plasmid vector for the introduction of DNA into plant cells without alteration of their normal regeneration capacity.* The EMBO Journal, vol. 2, No. 12, pp. 2143-2150, 1983.

Davin, Laurence B. et al., "Dirigent Proteins and Dirigent Sites Explain the Mystery of Specifity of Radical Precursor Coupling in Lignan and Lignin Biosynthesis," Plant Physiology, vol. 123, pp. 453-461, Jun. 2003.

Kim, Myoung K. et al.., "The western red cedar (*Thuja plicata*) 8-8' DIRIGENT family displays diverse expression patterns amd conserved monolignol coupling specifity," Plant Molecular Biology, pp. 199-214, 2002.

Gang, David R., "Regiochemical control of monolignol radical coupling: a new paradigm for lignin and lignan biosynthesis," Research Ppare, pp. 143-151, 1999.

Waterhouse, Peter M., "Virus Resistance and gene silencing in plants can be induced by simultaneous expression of sense and antisense RNA," Plant Biology, vol. 95, pp. 13959-13964, 1998.

Notification of the International Search Report and Written Opinion for PCT/US04/00113, 7 pages, mailed Dec. 7, 2005.

Jacinto, Tania et al., *Tomato prosystemin promoter confers wound-inducible, vascular bundle-specific expression of the β-glucuronidase gene in transgenic tomato plants.* Planta, vol. 203, pp. 406-412, 1997.

Rosahl, S., *Expression of a tuber-specific storage protein in transgenic tobacco plants: demonstration of an exterase activity,* The EMBO Journal, vol. 6, No. 5, pp. 1155-1159, 1987.

Kim, Younghee et al., "A 20 nucleotide upstream element is essential for the nopaline synthase (nos) promoter activity," Plant Molecular Biology, vol. 24, pp. 105-117, 1994.

Bildodeau, Pierre et al., "Far upstream activating promoter regions are responsible for expression of the BnC1 cruciferin gene from *Brassica napus*," Plant Cell Reports, vol. 14, pp. 125-130, 1994.

Kim, Seong-Ryong, "Identfication of Methyl Jasmonate and Salicylic Acid Response Elements from thwe Nopaline Synthase (nos) Promoter," Plant Physiol, vol. 103, pp. 97-103, 1993.

Baldwin, Don et al., "A comparison of gel-based nylon filter and microarray techniques to detect differential RNA expression in plants," Current Opinion in Plant Biology, vol. 2, pp. 96-103, 1999.

PCT International Search Report PCT/US04/00115, 7 pages, mailing date Jan. 5, 2004.

* cited by examiner

FIGURE 1

● Equally expressed in both tissues
● Expressed higher in stem than in leaf
● Expressed higher in leaf than in stem

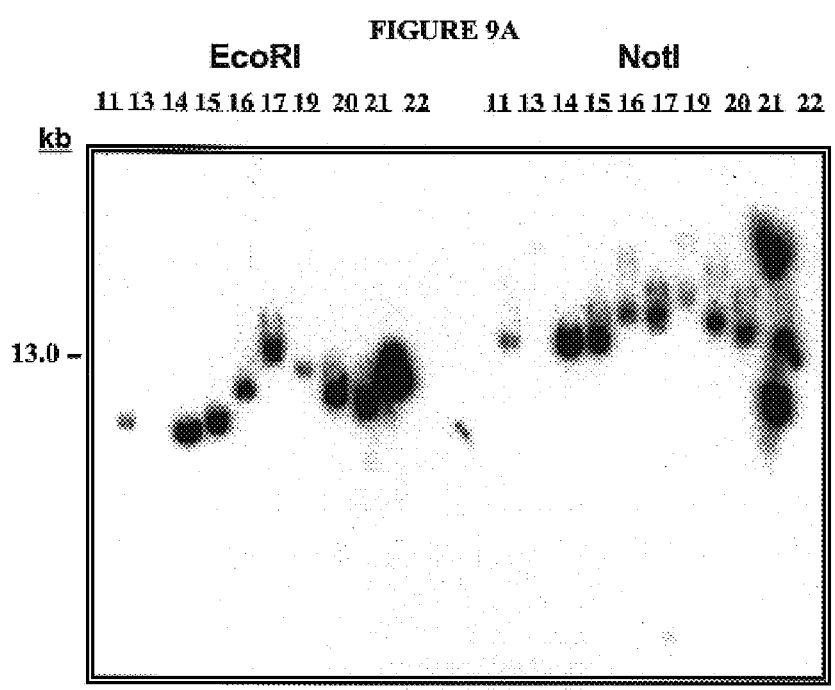

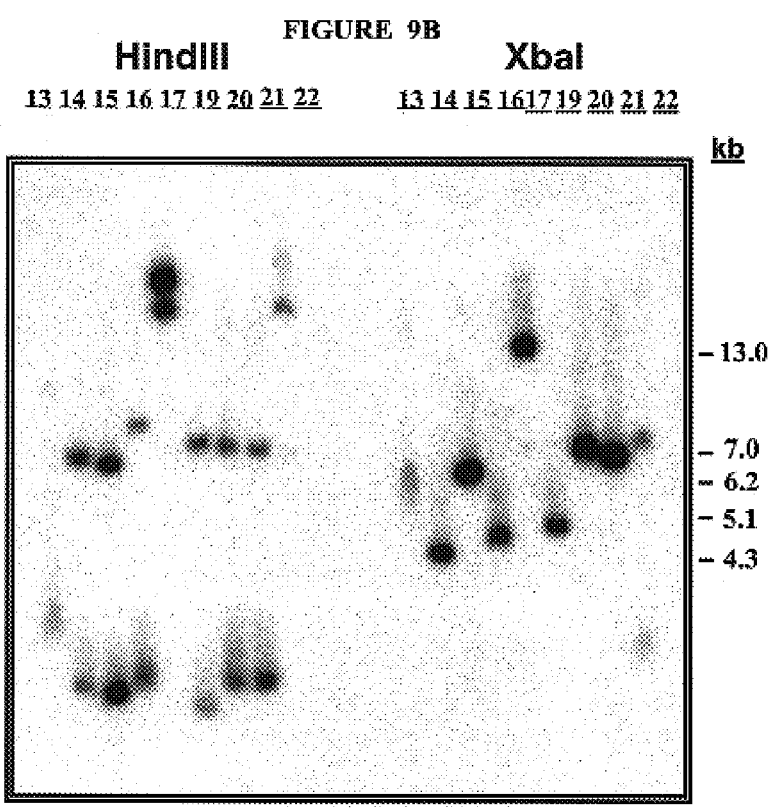

FIGURE 14
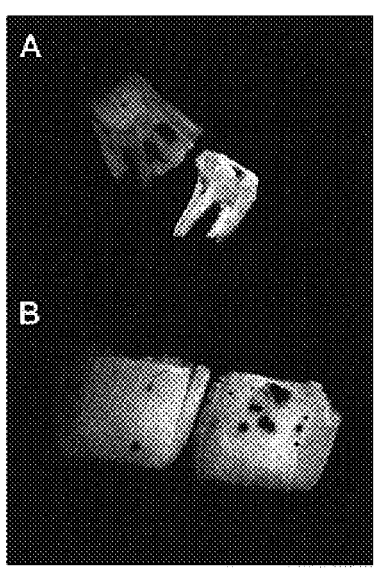 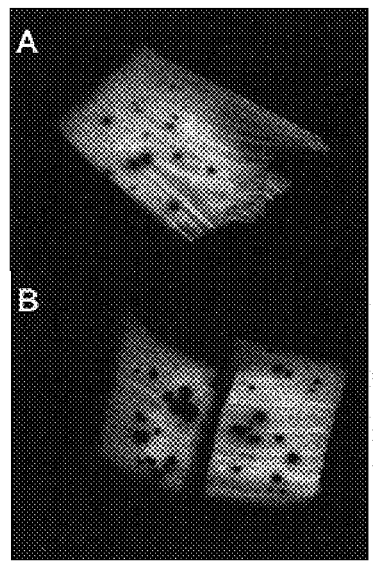

STEM-REGULATED, PLANT DEFENSE PROMOTER AND USES THEREOF IN TISSUE-SPECIFIC EXPRESSION IN MONOCOTS

PRIORITY CLAIM

The present invention claims priority under 35 U.S.C. §119(e) to U.S. Provisional Pat. Appln. Ser. No. 60/437,890 filed on Jan. 3, 2003 and titled "Plant Defense Gene Promoter for Tissue-Specific Expression in Monocots".

FIELD OF THE INVENTION

The present invention relates to the fields of plant functional genomics, molecular biology and genetic engineering, and specifically to selective regulation of gene expression in plants. In particular, the present invention relates to novel isolated nucleic acids having promoters capable of conferring stem-regulated expression and operable in plant defense. The promoters may be used in monocots, including polyploid species, to direct stem-regulated or defense-inducible expression of a heterologous gene.

BACKGROUND

A critical component of agriculture biotechnology is the use of highly regulated promoters to express agronomically important genes in crop plants so that genes of interest are expressed at optimal levels in appropriate tissues.

Monocots form a substantial portion of the world's food supply. Sugarcane is considered as one of the major worldwide crop for sugar supply with a net value of $20 billion per year. This crop could benefit from biotechnology approaches to engineer plants for disease, pest and herbicide resistance as well as improved sugar yield. However, compared to other major crops, there has been little research in developing sugarcane specific technologies such as genes and promoters that are functional in sugarcane. At the present time, there are no public-domain sugarcane promoters available for use in sugarcane transformation.

The selection of a promoter is often a critical factor in determining when and where within the plant the gene of interest is expressed.

A number of gene promoters that drive high levels of constitutive transgene expression are available for monocot plants. These include the maize ubiquitin promoter (Quail et al., 1996, U.S. Pat. No. 5,510,474), the rice actin1 promoter (McElroy and Wu, 1997, U.S. Pat. No. 5,641,876), various enhanced cauliflower mosaic virus (CaMV) 35S promoters (Mitsuhara et al., 1996, Plant Cell Physiol. 37:49-59) and promoters isolated from banana streak virus (Schenk et al., 2001, Plant Mol. Biol. 47:399-412). Promoters that have been isolated so far from sugarcane correspond to two polyubiquitin genes and confer constitutive gene expression in non-host plants such as rice (Wei et al., 1999, J. Plant Physiol. 155:513-519; Wei et al., 2003, J. Plant Physiol. 160:1241-1251).

Constitutive promoters may be suitable for the production of a desired protein in large quantities in all tissues of the plant throughout development. The energy requirements for high level constitutive production of the protein are often so great that other normal plant growth processes are compromised. For example, expression of a protein in a non-tissue specific manner as directed by a constitutively active promoter has often resulted in slow-growing or dwarfed plants. Even though providing constitutive expression of a gene is often desirable, it is also desirable in many instances to direct high expression of a gene to particular tissues and/or time of development in a plant. Tissue-specific promoters are capable of selectively expressing an introduced gene in desired tissues. Tissue-specific promoters may also be inducible, e.g. activated by internal or external agents such as phytohormones or defense inducing agents.

Restricting expression of the target protein to a particular tissue or organ or to specific events triggered when the plant is challenged with an external agent may be desirable to minimize possible toxic effects of some 'agronomic' gene products and to optimize overall plant growth and production. Furthermore, it is increasingly clear that promoter function varies from species to species. Thus it is essential to have promoters which are expressed specifically in target tissues of specific plants in order to genetically engineer plants.

Several promoters are currently being used for tissue-specific, heterologous gene expression in monocots. For example, the promoter regions from genes coding for hydrolases (β-glucanase), cysteine protease inhibitors (cystatin-1) or glucosidases (α-glucosidase) have been used to direct germination-specific expression of a heterologous DNA sequence in transgenic barley cells and kernels (Wolf, 1992, Mol. Gen. Genet. 234:33-42; Jensen et al., 1996, Proc. Natl. Acad. Sci. USA 93:3487-3491; Mikkonen et al., 1996, Plant Mol. Biol. 31:239-254; Jensen et al., 1998, U.S. Pat. No. 5,712,112; Lok et al., 2002, U.S. Pat. No. 6,359,196). The promoter for the glutamine synthetase gene has been also used to drive tissue-specific expression within the developing kernels of transgenic maize plants (Muhitch et al., 2002, Plant Science 163:865-872). Xylem- and phloem-specific promoters that are active in rice have also been reported, including the rice tungro baciliform virus and peroxidase gene promoters (Yin et al., 1997, Plant Journal 12:1178-1188; Ito et al., 2000, Plant Science 155:85-100); however it is not clear whether these promoters are active in other monocots, such as maize, sorghum and sugarcane. Furthermore, none of the above reported promoters are stem-regulated, which may be significant for crops such as sugarcane where the stem holds a large portion of the commercial value of the plant.

SUMMARY OF THE INVENTION

The present invention provides regulatory sequences which direct stem-regulated or defense-inducible expression and include novel promoters from a stem-expressed defense-inducible gene designated o-methyl transferase (OMT). The subject promoters may have specific advantages over the currently available tissue-specific promoters in their enhanced specificity in regulating gene expression in stem tissues and in response to induction by external stimuli such as plant defense-inducing agents. The subject promoters may be very useful in strategies aimed at altering carbon metabolism in the sucrose accumulating tissues, and for driving expression of insecticidal proteins in sugarcane. These promoters may also be applied to the development of improved pest and disease tolerant rice plants.

The present invention is directed to isolated nucleic acids including promoters operable primarily in the stem or in response to stimulation by defense-inducing agents. The subject promoters hybridize under stringent conditions to a promoter isolated from sugarcane, designated the OMT promoter, which promoter has the nucleotide sequence as set forth in SEQ ID NO: 1

In other embodiments of the invention, the subject isolated nucleic acids include promoters which direct stem-regulated or defense-inducible expression and have a sequence identity (sequence similarity) of from about 60% to about 65%, from about 65% to about 75%, from about 75% to about 85%, or from about 85% to about 90% when compared to the nucleotide sequence of the OMT promoter as set forth in SEQ ID NO. 1. Promoters of the present invention may also have a sequence identity of at least 60%, at least 70%, at least 80%, at least 90%, at least 95%, or at least 98% when compared to the OMT promoter of SEQ ID NO 1. It will be understood by one skilled in the art that where the designation "OMT promoter" is used in the present specification, use of other nucleic acids having hybridization characteristics or homologous sequences as set forth above may be appropriate as well unless a specific identity or sequence is clearly indicated.

However, all OMT promoters retain some ability to direct stem-specific transcription or defense-inducible transcription.

In a further embodiment, the present invention is directed to an isolated nucleic acid having a promoter which directs stem-regulated or defense-inducible expression, which promoter has the nucleotide sequence as set forth in SEQ ID NO:1.

Other embodiments of the invention include expression vectors including an isolated nucleic acid having a promoter which directs stem-regulated or defense-inducible expression, including an OMT promoter. The expression vector may, more specifically, be transferred into a plant cell to be transformed in such a manner as to allow expression of an encoded protein in tissues derived from the plant cell. The vector may also transmitted into the plant cell in such a manner as to allow inheritance of the nucleic acid into the second progeny of plants generated from a plant derived from the transformed plant cell. More specifically, such inheritance may be Mendelian. Examples of plant transformation expression vectors including the OMT promoter are shown in FIGS. 2 and 3.

In still another embodiment, the present invention may be directed to cells, tissues and plants transformed with an expression vector including an isolated nucleic acid having a promoter which directs stem-regulated or defense-inducible expression, including an OMT promoter, and the progeny generated from such transformed plants. In specific embodiments, the plant may be a monocot, such as maize, rice, sugarcane or sorghum.

In still further embodiments, the present invention provides an expression cassette which includes an isolated nucleic acid having a promoter which directs stem-regulated or defense-inducible expression including an OMT promoter operably linked to a heterologous gene or a nucleic acid encoding a sequence complementary to the native plant gene and vectors containing such expression cassettes.

The present invention also includes methods for directing stem-regulated expression in a tissue or plant by providing such tissue or plant with an isolated nucleic acid having a promoter including an OMT promoter to effect such stem-regulated expression. Other methods relate to directing defense-inducible expression in a plant by providing such plant with an isolated nucleic acid having a promoter including an OMT promoter to effect such defense-inducible expression.

BRIEF DESCRIPTION OF THE DRAWINGS

Specific embodiments of the present invention are further described in the following detailed description taken in conjunction with the accompanying drawings. The file of the present patent contains at least one drawing executed in color as determined by the U.S. Pat. and Trademark Office. Copies of this patent with color drawing(s) will be provided by the Patent and Trademark Office upon request and payment of the necessary fees.

FIG. 1 depicts, according to an embodiment of the present invention, the nucleotide sequence of a 3.012 kb fragment (SEQ ID NO:1) of the o-methyl transferase gene (OMT) which lies immediately upstream of the putative translational start site. The putative TATA box, CAT box sequence and first ATG are bolded.

FIG. 9 is a DNA gel blot analysis of restriction digests of ten OMT positive genomic clones probed with OMT full-length cDNA.

FIG. 14 is a photomicrograph of particle bombarded maize and sorghum stem tissues showing histochemical localization of transient GUS expression driven by the stem-regulated OMT promoter or the constitutive maize ubiquitin1 promoter.

DETAILED DESCRIPTION

Figure 2:
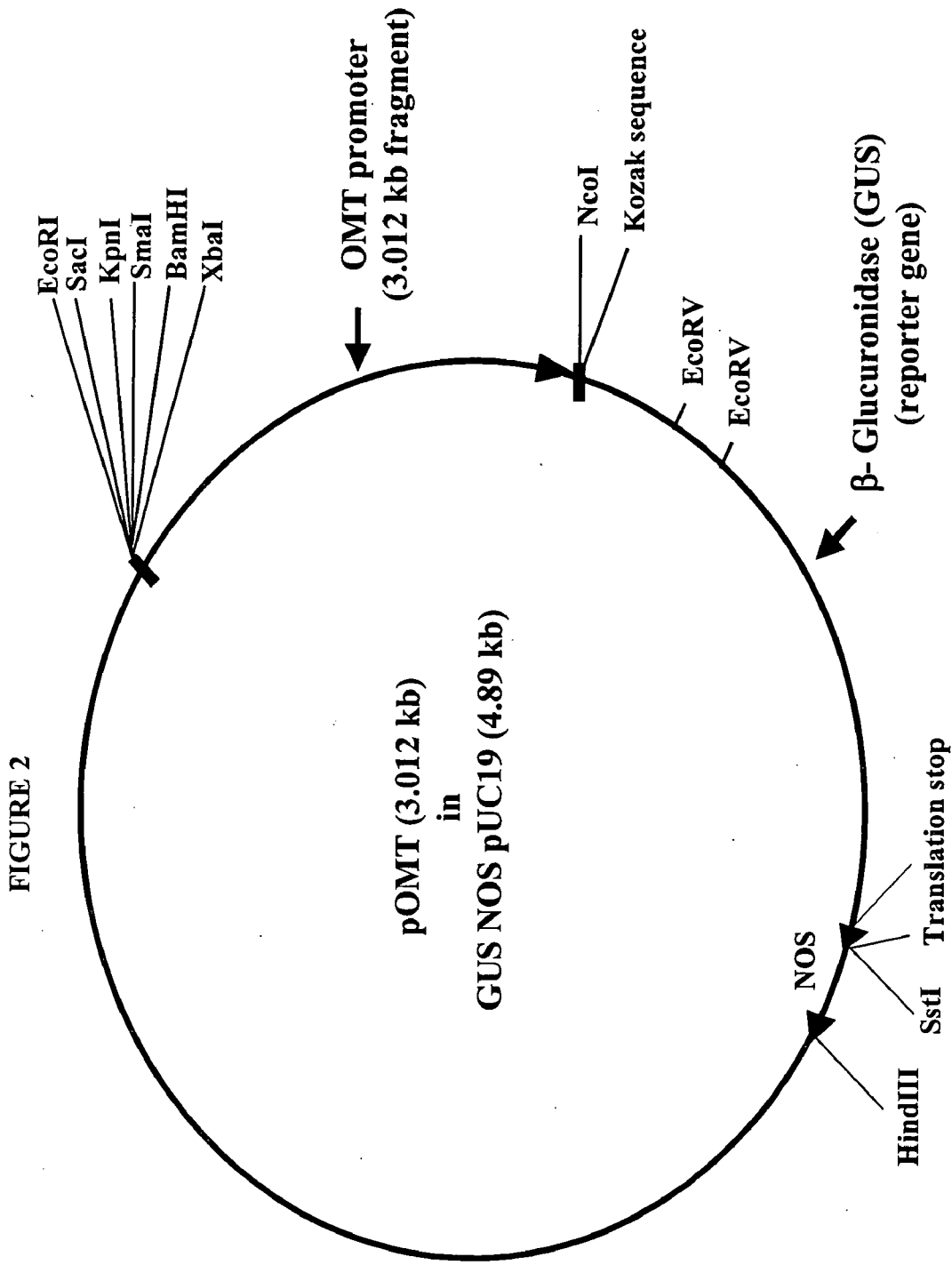
FIG. 2 illustrates, according to an embodiment of the present invention, the OMT promoter/GUS expression vector (pOMT::GUSpUC19) suitable for expression in sugarcane, maize and sorghum.

The present invention includes isolated nucleic acids having promoters capable of directing specific expression in stem tissue or operable in response to stimulation by defense-inducing agents. In accordance with the present invention, a subject promoter, when operably linked to either the coding sequence of a gene or a sequence complementary to a native plant gene, directs expression of the coding sequence or complementary sequence in stem tissue or in response to a defense-inducing agent.

Figure 1:
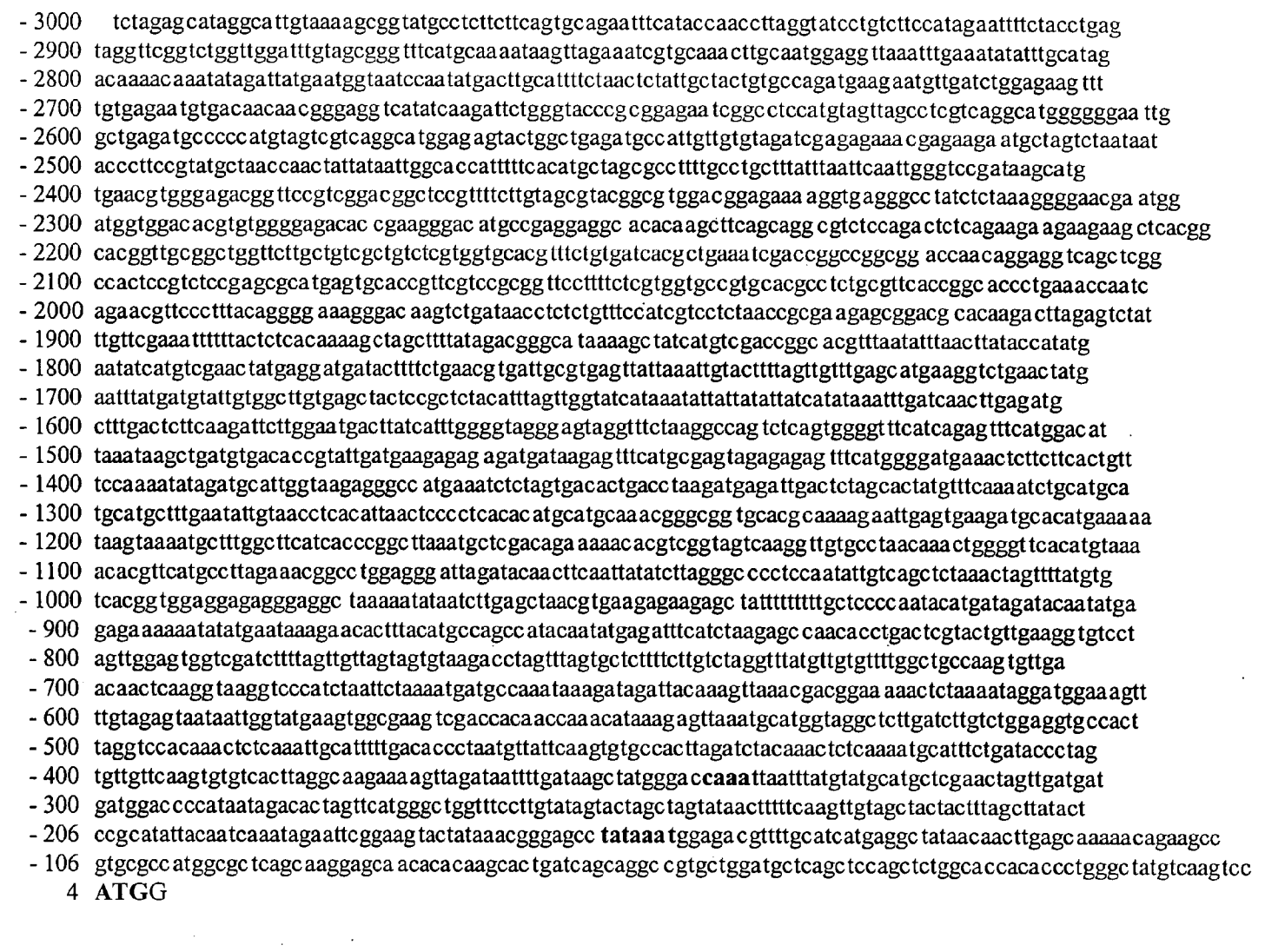

In one embodiment of the present invention, there is provided an isolated nucleic acid corresponding to a promoter isolated from a sugarcane stem-regulated, defense-inducible gene, designated o-methyl transferase (OMT) promoter, having the sequence of nucleotides −3012 to −1 as depicted in FIG. 1 (nucleotides 1 to 3012 of SEQ ID NO:1).

The promoters of the present invention are useful in the construction of expression cassettes which include, in the 5' to 3' direction, a promoter which directs stem-regulated or defense-inducible expression such as the OMT promoter, a heterologous gene or a coding sequence, or sequence complementary to a native plant gene under control of the promoter, and a 3' termination sequence. Such an expression cassette may be incorporated into a variety of autonomously replicating vectors in order to construct an expression vector.

In one embodiment of the present invention, there is provided a promoter from a sugarcane OMT gene. An isolated nucleic acid for a promoter from an OMT gene can be provided as follows. OMT recombinant genomic clones are first isolated by screening a sugarcane genomic bacterial artificial chromosome (BAC) library with a cDNA (or a portion thereof) representing OMT mRNA. In order to obtain a cDNA representing OMT mRNA, a sugarcane stem-regulated cDNA library may be constructed and screened by differential hybridization with stem, leaf and root cDNA probes to identify stem-regulated cDNAs including the OMT cDNA.

Methods considered useful in obtaining genomic recombinant DNA sequences corresponding to the OMT gene by screening a genomic library are provided in Sambrook et al. (1989), Molecular Cloning: A Laboratory Manual, Cold Spring Harbor, N.Y., for example, or any of the laboratory manuals on recombinant DNA technology that are widely available.

To determine nucleotide sequences, a multitude of techniques are available and known to the ordinarily skilled artisan. For example, restriction fragments containing a corresponding OMT gene may be subcloned into the polylinker site of a sequencing vector such as pBluescript (Stratagene). These pBluescript subclones may then be sequenced by the double-stranded dideoxy method (Chen et al. (1985) DNA, 4; 165).

In a specific embodiment of the present invention, the OMT promoter includes nucleotides −3012 to −1 of FIG. 1 (nucleotides 1 to 3012 of SEQ ID NO:1).

Modifications to the OMT promoter as set forth in SEQ ID NO:1, which maintain the characteristic property of directing stem-regulated or defense-inducible expression, are within the scope of the present invention. Such modifications include insertions, deletions and substitutions of one or more nucleotides.

The subject OMT promoter may be derived from restriction endonuclease or exonuclease digestion of isolated OMT genomic clones. Thus, for example, the known nucleotide or amino acid sequence of the coding region of a gene of the o-methyl transferase gene family is aligned to the nucleic acid or deduced amino acid sequence of an isolated stem-regulated genomic clone and the 5' flanking sequence (i.e., sequence upstream from the translational start codon of the coding region) of the isolated OMT genomic clone is located.

The OMT promoter as set forth in SEQ ID NO:1 (nucleotides −3012 to −1 of FIG. 1) may be generated from genomic clones having either or both excess 5' flanking sequence or coding sequence by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base"® system. Alternatively, PCR primers may be defined to allow direct amplification of the subject OMT promoter.

Using the same methodologies, the ordinarily skilled artisan may generate one or more deletion fragments of the OMT promoter as set forth in SEQ ID NO:1. Any and all deletion fragments which include a contiguous portion of the nucleotide sequences set forth in SEQ ID NO:1 and which retain the capacity to direct stem-regulated or defense-inducible expression are contemplated by the present invention.

In addition to the sugarcane OMT promoter having the nucleotide sequence set forth as −3012 to −1 in FIG. 1 (SEQ ID NO:1), the present invention is directed to other promoter sequences which correspond to the same gene, i.e., a homolog, in other plant species. As defined herein, such related sequences which direct stem-regulated or defense-inducible expression, may be described in terms of their percent homology or identity on a nucleotide level to the nucleotide sequence (−3012 to −1) as set forth in FIG. 1 (nucleotides 1 to 3012 of SEQ ID NO:1). Alternatively, such related sequences from other plant species may be defined in terms of their ability to hybridize to the OMT promoter of SEQ ID NO: 1 under stringent hybridization conditions.

The present invention therefore contemplates nucleic acid sequences hybridizing with the OMT nucleic acid sequence as set forth in FIG. 1 (SEQ ID NO:1) and which differ in one or more positions in comparison with SEQ ID NO:1 so long as such hybridizing sequence corresponds to a promoter which directs stem-regulated or defense-inducible expression.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)). An example of one such stringent hybridization condition is hybridization in 4×SSC at 65° C., followed by a washing in 0.1×SSC at 65° C. for one hour. Alternatively, an exemplary stringent hybridization condition is in 50% formamide, 4×SSC at 42° C.

Promoter sequences of the present invention may also be described in terms of percent homology or identity on a nucleotide level to the nucleotide sequence −3012 to −1 depicted in FIG. 1 (nucleotides 1 to 3012 of SEQ ID NO:1). There are a number of computer programs that compare and align nucleic acid sequences which one skilled in the art may use for purposes of determining sequence identity (sequence similarity).

Thus, an isolated nucleic acid is provided having a promoter which directs stem-regulated or defense-inducible expression and has a sequence identity (sequence similarity) of about 60% to about 65% when compared to the nucleotide sequence of the OMT promoter as set forth in SEQ ID NO:1. In a specific embodiment, an isolated nucleic acid including a promoter which directs stem-regulated expression has a sequence identity (sequence similarity) of about 65% to about 75% when compared to the sequence of the OMT promoter as set forth in SEQ ID NO:1.

In another specific embodiment, an isolated nucleic acid including a promoter which directs stem-regulated expression has a sequence identity (sequence similarity) of about 75% to about 85% when compared to the sequence of the OMT promoter as set forth in SEQ ID NO:1.

In another specific embodiment, an isolated nucleic acid including a promoter which directs stem-regulated expression has a sequence identity (sequence similarity) of about 85% to about 90% when compared to the sequence of the OMT promoter as set forth in SEQ ID NO:1.

In another specific embodiment, an isolated nucleic acid including a promoter which directs stem-regulated expression has a sequence identity (sequence similarity) of about 90% or greater when compared to the sequence of the OMT promoter as set forth in SEQ ID NO:1.

Sequences similar to a subject promoter may be identified by database searches using the promoter or elements thereof as the query sequence using the Gapped BLAST algorithm (Altschul et al., 1997 Nucl. Acids Res. 25:3389-3402) with the BLOSUM62 Matrix, a gap cost of 11 and persistence cost of 1 per residue and an E value of 10. Two sequences may be compared with either ALIGN (Global alignment) or LALIGN (Local homology alignment) in the FASTA suite of applications (Pearson and Lipman, 1988 Proc. Nat. Acad. Sci. 85:2444-24448; Pearson, 1990 Methods in Enzymology 183:63-98) with the BLOSUM50 matrix and gap penalties of −16, −4.

Nucleic acid molecules corresponding to promoters of the present invention may be obtained by using the subject 3.012 kb OMT promoter of SEQ ID NO: 1 or a portion thereof (including fragments) or complements thereof as a probe and hybridizing with a nucleic acid molecule(s) from any higher plant. Nucleic acid molecules hybridizing to the 3.012 kb OMT promoter or a portion thereof can be isolated, e.g., from genomic libraries by techniques well known in the art. Promoter fragments homologous to OMT may also be isolated by applying a nucleic acid amplification technique such as the polymerase chain reaction (PCR) using as primers oligonucleotides derived from sequence set forth in SEQ ID NO:1.

Confirmation of the stem-specificity or defense-inducibility of the OMT promoter (including modifications or deletion fragments thereof), and promoters from homologous genes which direct stem-regulated or defense-inducible expression, may be accomplished by construction of transcriptional and/or translational fusions of specific sequences with the coding sequences of a heterologous gene or coding sequence, transfer of the expression cassette into an appropriate host, and detection of the expression of the heterologous gene or coding sequence. The assay used to detect expression depends upon the nature of the heterologous gene or coding sequence. For example, reporter genes, exemplified by chloramphenicol acetyl transferase and β-glucuronidase (GUS), are commonly used to assess transcriptional and translational competence of chimeric nucleic acids. Standard assays are available to sensitively detect the reporter enzyme in a transgenic organism.

The GUS gene is useful as a reporter of promoter activity in transgenic plants because of the high stability of the enzyme in plant cells, the lack of intrinsic GUS activity in higher plant cells and availability of a quantitative fluorimetric assay and a histochemical localization technique. Jefferson et al. (1987) (EMBO J. 6: 3901-3907) have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such expression cassettes allows definition of specific regulatory sequences and demonstrates that these sequences can direct expression of heterologous genes, or coding sequences in a stem-regulated or defense-inducible manner.

Another aspect of the invention is directed to expression cassettes and expression vectors including a promoter which directs stem-regulated or defense-inducible expression such as an OMT promoter or portion thereof, operably linked to the coding sequence of a heterologous gene such that the regulatory element is capable of controlling expression of the product encoded by the heterologous gene. The heterologous gene can be any gene other than OMT. If necessary, additional regulatory elements from genes other than OMT or parts of such elements sufficient to cause expression resulting in production of an effective amount of the polypeptide encoded by the heterologous gene may be included in the expression cassettes.

As used herein, the term "cassette" refers to a nucleotide sequence capable of expressing a particular coding sequence if said coding sequence is inserted so as to be operably linked to one or more regulatory regions present in the nucleotide sequence. Thus, for example, the expression cassette may include a heterologous coding sequence which is desired to be expressed in a plant seed. The expression cassettes and expression vectors of the present invention are therefore useful for directing stem-regulated or defense-inducible expression of any number of heterologous genes.

Accordingly, the present invention provides expression cassettes including sequences of a promoter which directs stem-regulated or defense-inducible expression including the OMT promoter which are operably linked to a heterologous gene such as a sugar transport gene or sugar accumulation gene. Examples of sugar transport genes useful for practicing the present invention include sucrose transporters and other monosaccharide and disaccharide transporters. Such sugar transporter genes have been isolated and characterized from sugarcane and other plant species. Their nucleotide coding sequences as well as methods of isolating such coding sequences are disclosed in the published literature and are widely available to those of skill in the art.

Additionally, the present invention includes expression cassettes which express products having an insecticidal or antimicrobial activity. Introduction into a plant cell of a expression cassette including an insecticidal or antimicrobial gene operably linked to the subject promoter sequences such as the OMT promoter allows for protection in the stem. Examples of antimicrobial genes useful for practicing the present invention include chitinase and β-1,3-glucanase genes (Jach et al. 1995 Plant Journal 8:97-109). Expression cassettes which include the subject promoter such as the OMT promoter operably linked to a bioinsecticidal peptide or a defence elicitor peptide that upregulate the endogenous pathway are particularly contemplated to amplify natural defense responses.

The expression cassettes of the present invention may be constructed by ligating a subject promoter such as the OMT promoter or part thereof to the coding sequence of a heterologous gene. The juxtaposition of these sequences may be accomplished in a variety of ways. In one embodiment, the sequence order is in a 5' to 3' direction and includes an OMT promoter and coding sequence of a heterologous gene. In another the sequences order in a 5' to 3' direction is an OMT promoter, a coding sequence and a termination sequence which includes a polyadenylation site.

Standard techniques for construction of such expression cassettes are well known to those of ordinary skill in the art and can be found in references such as Sambrook et al. (1989). A variety of strategies are available for ligating fragments of DNA, the choice of which depends on the nature of the termini of the DNA fragments.

The restriction or deletion fragments that contain a subject promoter TATA box are ligated in a forward orientation to a promoterless heterologous gene or coding sequence such as the coding sequence of GUS. The skilled artisan will recognize that promoters of the present invention and parts thereof, may be provided by other means, for example chemical or enzymatic synthesis.

The 3' end of a heterologous coding sequence is optionally ligated to a termination sequence including a polyadenylation site, exemplified by, but not limited to, the nopaline synthase polyadenylation site, or the octopine T-DNA gene 7 polyadenylation site. Alternatively, the polyadenylation site may be provided by the heterologous gene or coding sequence.

The present invention also provides methods of increasing expression levels of heterologous genes or coding sequences in plant stem tissues. In accordance with such methods, the expression cassettes and expression vectors of the present invention may be introduced into a plant in order to effect expression of a heterologous gene or coding sequence. For example, a method of producing a plant with increased levels of a product of a sucrose accumulating gene or a defense gene is provided by transforming a plant cell with an expression vector including an OMT promoter or portion thereof, operably linked to a sucrose accumulating gene or a defense gene and regenerating a plant with increased levels of the product of the sucrose accumulating gene or defense gene. In a specific embodiment of the present invention, a transgenic sugarcane line may be produced in which the sugar metabolism is altered to increase its stem dry weight. This is of particular importance because commercial sugarcane varieties accumulate up to 50-60% of dry weight of their stem tissues as sucrose. In a further specific embodiment of the present invention, a transgenic sugarcane line may be produced with enhanced bioinsecticidal activity for protection against stem boring insects, which are the most destructive pests. Expression of the bioinsecticidal protein may be induced in this case by the application of a defense inducing agent such jasmonic acid.

Another aspect of the present invention provides methods of reducing levels of a product of a gene which is native to a plant which includes transforming a plant cell with an expression vector having an OMT promoter or part thereof, operably linked to a nucleic acid sequence which is complementary to the native plant gene. In this manner, levels of endogenous product of the native plant gene are reduced through a mechanism known as antisense regulation. Thus, for example, levels of a product of a sucrose accumulating gene or defense gene are reduced by transforming a plant with an expression vector including an OMT promoter or part thereof, operably linked to a nucleic acid sequence which is complementary to a nucleic acid sequence coding for a native sucrose accumulating gene or a defense gene.

The present invention also provides a method of silencing a gene native to a plant which includes transforming a plant cell with an RNAinterference (RNAi) expression vector including an OMT promoter or part thereof, operably linked to a nucleic acid sequence which is an inverted repeat of the native plant gene. In this manner, levels of endogenous product of the native plant gene are reduced through a mechanism known as RNA interference. Thus, for example, levels of a product of a sucrose synthesis gene may be reduced by transforming a plant with an expression vector including a subject stem-regulated promoter or part thereof, operably linked to a nucleic acid sequence which is an inverted repeat of the nucleic acid sequence coding for a native sucrose accumulating gene or a defense gene.

The present invention further provides a method of cosuppressing a gene which is native to a plant which includes transforming a plant cell with an expression vector having an OMT promoter or part thereof, operably linked to a nucleic acid sequence coding for the native plant gene. In this manner, levels of endogenous product of the native plant gene are reduced through the mechanism known as cosuppression. Thus, for example, levels of a product of a sucrose synthesis gene or defense gene may be influenced by transforming a plant with an expression vector including a subject promoter or part thereof, operably linked to a nucleic acid sequence coding for a sucrose accumulating gene or defense gene native to the plant. Although the exact mechanism of cosuppression is not completely understood, one skilled in the art is familiar with published works reporting the experimental conditions and results associated with cosuppression (Napoli et al. (1990) The Plant Cell, 2; 270-289; Van der Krol (1990) Plant Mol. Biol, 14; 457-466.)

Figure 3:
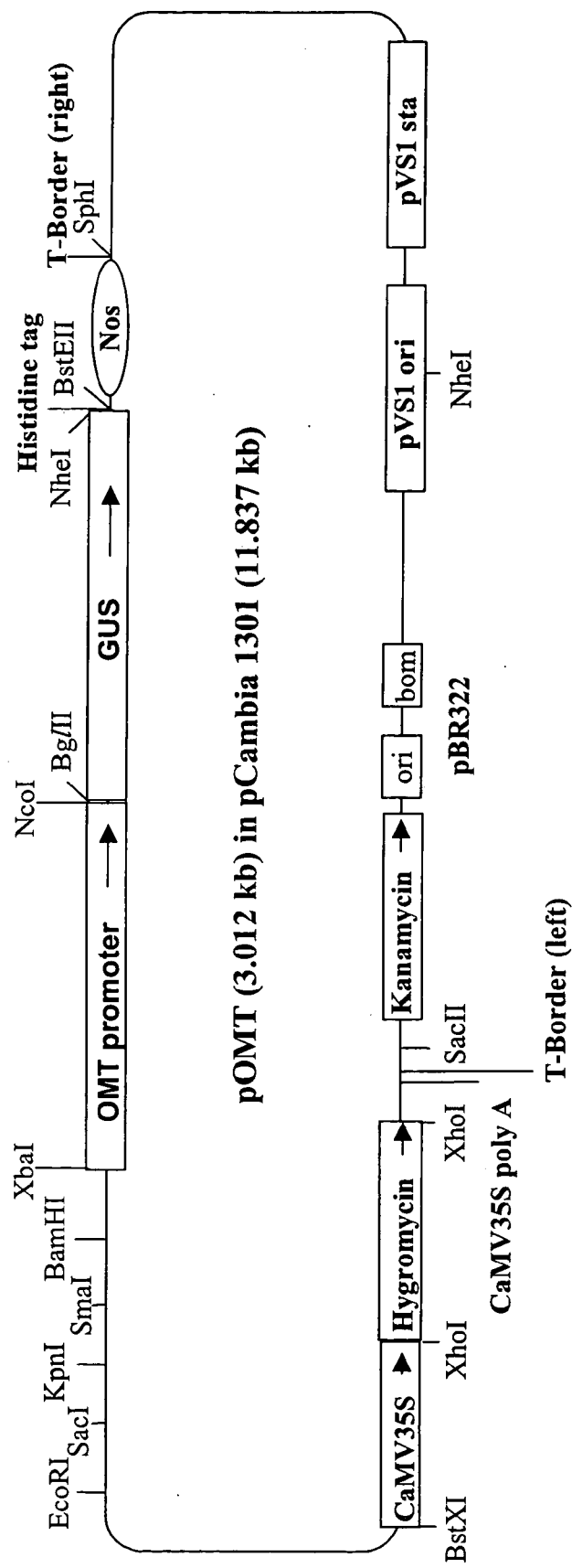
FIG. 3 illustrates, according to an embodiment of the present invention, the OMT promoter/GUS expression vector (pOMT::GUSpCambia) suitable for expression in rice.

To provide regulated expression of the heterologous or native genes, plants may be transformed with the expression cassette constructions of the invention. Methods of nucleic acid transfer are well known in the art. The expression cassettes may be introduced into plants by leaf disk transformation-regeneration procedure as described by Horsch et al. (1985) Science, 227; 1229-1231. Other methods of transformation such as protoplast culture (Horsch et al. (1984) Science, 223; 496; DeBlock et al. (1984) EMBO J., 2; 2143; Barton et al. (1983) Cell, 32; 1033) may also be used and are within the scope of this invention. In a specific embodiment, plants including rice and other monocots and dicots are transformed with Agrobacterium-derived vectors such as the pCambia vectors described in Maliga et al. (1994) (Plant Mol. Biol., 35; 989-994) (FIG. 3). In another specific embodiment, embryonic calli and plant organs are transformed by gene gun particle bombardment with the expression vector shown in FIG. 2.

In another specific embodiment, stem tissues and embryonic calli are particle bombarded using the gene gun/biolistic approach as described in (Klein et al. (1987) Nature, 327; 70). Other well-known methods are available to insert the expression cassettes of the present invention into plant cells. Such alternative methods include electroporation, chemically-induced DNA uptake, and use of viruses or pollen as vectors.

When necessary for the transformation method, the expression cassettes of the present invention may be inserted into a plant transformation vector, e.g. the binary vector described by Maliga et al. (1994) Plant Mol. Biol., 25; 989-994. Plant transformation vectors may be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Embryonic calli and and other susceptible tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in tissues, developing seeds, young seedlings and mature plants may be monitored by immunological, histochemical, mRNA expression or activity assays. As discussed herein, the choice of an assay for expression of the expression cassette depends upon the nature of the heterologous coding sequence. For example, RNA gel blot analysis may be used to assess transcription if appropriate nucleotide probes are available. If antibodies to the polypeptide encoded by the heterologous gene are available, Western analysis and immunohistochemical localization may be used to assess the production and localization of the polypeptide. Depending upon the heterologous gene, appropriate biochemical assays may be used.

Another aspect of the present invention provides transgenic plants or progeny of these plants containing the expression cassettes of the invention. Both monocot and dicot plants are contemplated. Plant cells may be transformed with the expression cassettes by any of the plant transformation methods described above. The transformed plant cell, usually in the form of a callus culture, leaf disk, explant or whole plant (via *Agrobacterium*-mediated transformation or gene gun particle bombardment) may be regenerated into a complete transgenic plant by methods well-known to one of ordinary skill in the art (e.g., Horsh et al., 1985). In a specific embodiment, the transgenic plant is sugarcane, rice, maize, sorghum or other monocot plant. Because progeny of transformed plants inherit the expression cassettes, seeds or cuttings from the transformed plants may be used to maintain the transgenic line.

EXAMPLES

The invention may be further understood through reference to the following examples, which provide further description of specific embodiments of the invention. Variations of these examples will be apparent to one skilled in the art and are intended to be encompassed in the present invention.

Example 1

Identification of Stem-Specific cDNAs

Stem-Specific cDNA Macroarray Analysis

To identify cDNAs that were expressed in sugarcane stems, a cDNA library representing stem mRNA was constructed and screened by differential hybridization.

In order to have a cDNA library that has a good representation of mRNA from all regions of the stem, mRNA was separately isolated from top, mid and bottom portions of the stem of *Saccharum* spp. cultivar CP72-1210 and a pooled sample was used for preparation of the cDNA. Total RNAs and poly(A)+ RNAs were prepared using the RNeasy kit and Oligotex kit from Qiagen, respectively. For the synthesis of cDNAs, the SMART PCR cDNA library construction kit (BDBiosciences Clontech) was selected since this technology utilizes a unique SMART oligonucleotide (cap finder) in the first strand cDNA synthesis followed by a long distance PCR (LD PCR) amplification to generate high yields of full-length ds cDNAs. A pooled sample consisting of 100 ng of each of stem top, mid and bottom poly(A)+ RNAs was used for the preparation of first strand cDNAs which were then selected to synthesize ds cDNAs by LD PCR. The sizes of ds cDNA ranged from 300 bp to 6 kb. To eliminate small and partial (less than full-length) cDNAs, the ds cDNA sample was subjected to gel fractionation and the agarose gel slice containing 500 bp to 3 kb was excised and purified. This selected cDNA fraction was cloned into pCR2.1 vector (TA cloning kit, Invitrogen) using DH10B *Escherichia coli* bacterial cells for transformation. The ampicillin-resistant and white colonies were picked and archived in 384-well microtiter plates. A total of 13,824 cDNA clones (archived in thirty six 384-well microtiter plates) were obtained. About 100 clones were randomly picked, and DNA preparations were made and tested by restriction analysis to reveal insert sizes of 300 bp to 1500 bp.

Figure 4:
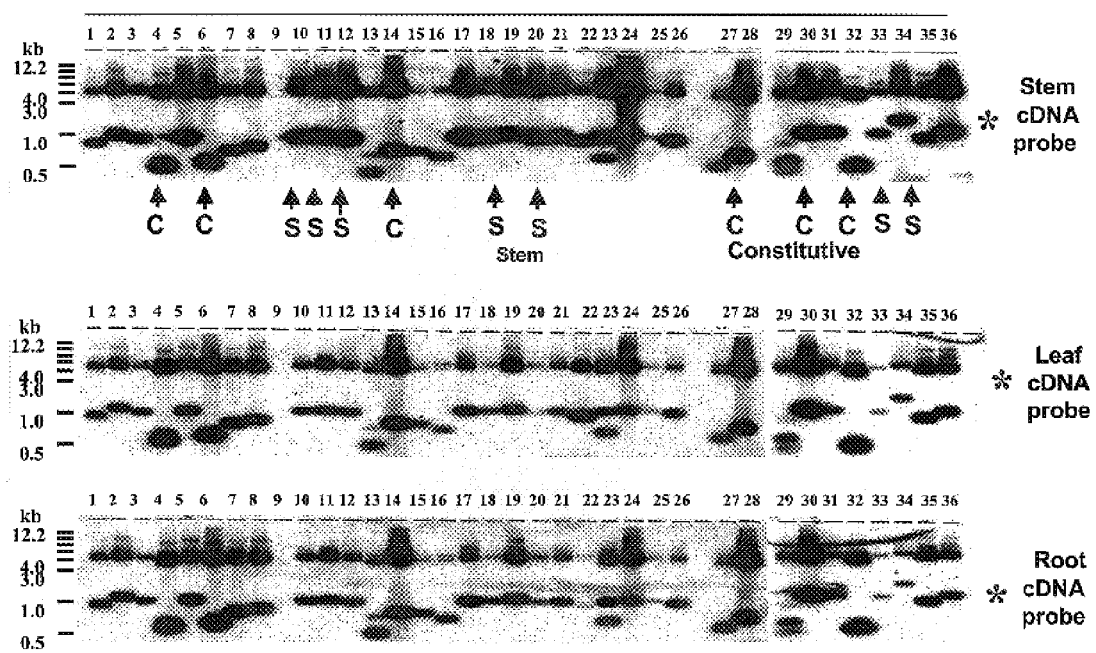
FIG. 4 is a DNA gel blot analysis of restriction digests of 36 stem-regulated cDNA clones probed separately with cDNA from five sugarcane tissues, stem (top, middle and bottom), leaf and root.

Next the cDNA library was screened using differential hybridization to identify stem-specific cDNAs. Specifically, macroarrays consisting high density replica filters (three copies: A, B and C) of the library were prepared using a 3×3 duplicate grid pattern using a Beckman Biomek 2000. Each copy of the library (9 filters) was first probed with radioactively-labeled (random decamer priming method; Decaprime II kit, Ambion) cDNA of top, mid and bottom stem tissues, respectively. Hybridization were carried out at 65.degree.C. and blots were washed up to the final stringency of 0.3.times.SSC/0.1.percen.SDS and exposed to X-ray films. After the autorads from these hybridizations were obtained, filters of copies A and B were stripped and hybridized with 32P-labeled cDNA probes of leaf and root tissues, respectively. Both strong and weak hybridization signals were recorded with an intention of identifying cDNAs that are strongly expressed in one type of tissue but weak in all others and vice versa. Using this strategy, information from all possible combinations (stem top vs root, stem mid vs leaf, stem mid vs root, stem bottom vs leaf, stem bottom vs root, stem top vs stem mid, stem top vs stem bottom, stem mid vs stem bottom and leaf vs root) was gathered. Data obtained from these substractions revealed that a total of 188 cDNAs were present specifically in stem and 41 cDNAs displayed constitutive expression. To further corroborate the expression patterns of these cDNA clones, DNA gel blots were prepared using restriction digests of 36 selected clones and probed with radioactively-labeled cDNA from five tissues separately. Based on these analyses, 25 clones displayed stem-specific expression and 11 cones showed constitutive expression (See FIG. 4).

Stem-Specific cDNA Microarray Analysis

Figure 5:
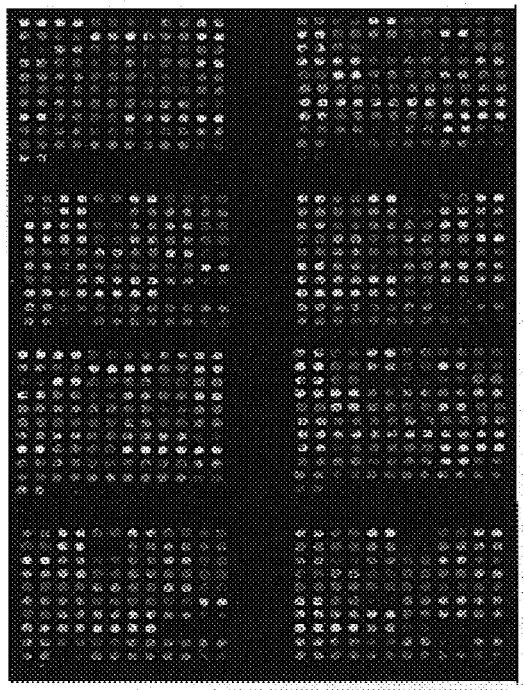
FIG. 5 is an image of a sugarcane cDNA microarray after hybridization.
Figure 6:
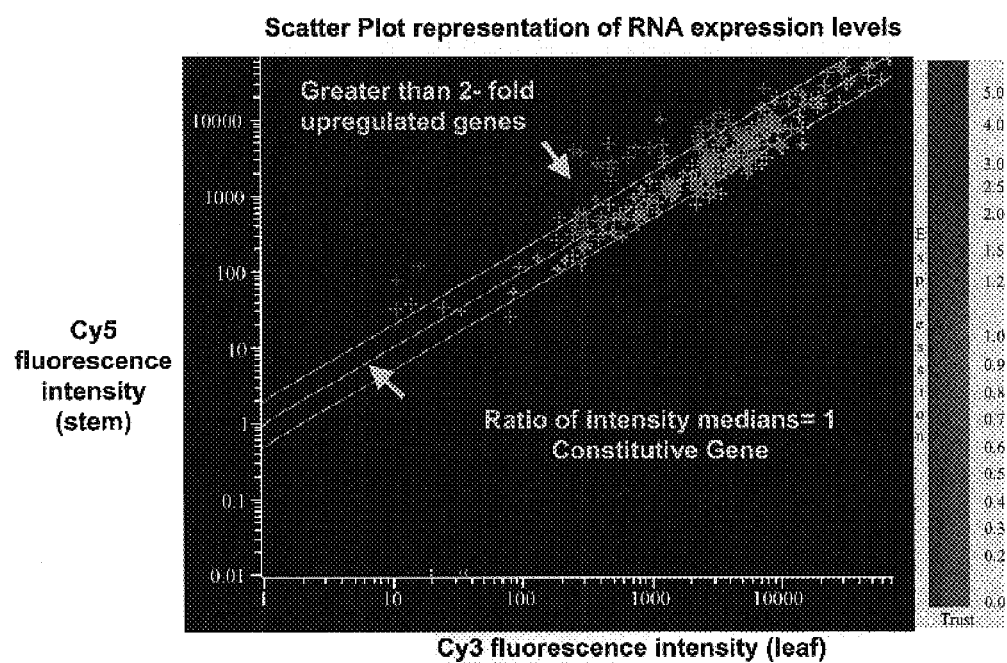
FIG. 6 is a scatter plot representation of RNA expression levels of 251 sugarcane cDNA clones as detected by the microarray analysis.

The macroarray analysis of the potential stem-specific CAN clones was followed by a focused microarray analyis. A DNA microarray including the panel of the 188 stem-specific cDNA clones initially identified by the macroarray analysis along with 63 additional cDNA clones was constructed to provide a sensitive assessment of their differential RNA expression profiles. Amplified PCR products for the 251 cDNAs were printed in duplicate on glass microscope slides using a gridding robot from Genemachines. The resulting microarray was probed with fluorescently labeled cDNAs synthesized from 1.mu.g of total amplified RNA (MessageAmp aRNA kit from Ambion for RNA amplification). One cDNA probe (e.g. stem RNA) is labeled with one dye (Cy5), and the second (e.g. leaf or root RNA) with another dye (Cy3) using the 3DNA Array 350RP expression array detection kit of Genisphere and based on the two-color fluorescent hybridization microarray system developed by Brown and colleagues at Stanford (Derisi et al. 1996 Science 278:680-686). The two probes labeled with distinct dyes were hybridized simultaneously to a single DNA array to allow for comparison of two different RNA populations or internal standardization. Hybridization was detected and quantified with a confocal laser scanner (Affynetrix) that captures the image of the emission wavelength of each dye. A combined image of the microarray hybridized with fluorescent probes representing stem RNA and leaf RNA is shown in FIG. 5. The resulting digital data was analyzed with the GenePix analysis software (Axon) and GeneSpring analysis software (Silicon Genetics). FIG. 6 shows a scatter plot representation of the RNA expression levels of the 251 cDNA clones of the microarray after hybridization with probes from stem and leaf RNAs. Each '+' symbol represents a cDNA. The normalized abundance of each cDNA derived from stem RNA (Cy5) (y axis) was plotted vs that derived from leaf RNA (Cy3) (x axis). Data were normalized using the endogenous constitutive gene ubiquitin. The central magenta line indicates equal hybridization of both Cy5 and Cy3 probes. The outer magenta line indicates expression levels of genes that are two-fold up or down.

Among the 251 cDNAs examined in the microarray analysis, 41 appeared to be at least two-fold upregulated in the stem, whereas 14 were constitutively expressed.

The 41 stem-upregulated cDNAs were sequenced using the cycle sequencing with ABI PRISM dye terminator cycle sequencing kit and ABI 377 automated DNA sequencer. Database searches for homologous nucleic acids were performed through NCBI using the BLAST algorithm. Several of the 41 stem-upregulated cDNA clones were found to belong to multigene families. One cDNA that exhibited a 3.2-fold upregulation shared significant sequence similarity to a monocot gene involved in defense pathways, o-methyl transferase (OMT). In maize, OMT is a key enzyme in the biosynthetic pathway of phenolic compounds (Held, B. M. et al. 1993 Plant Physiol. 102:1001-1008). It is induced by fungal pathogens and other stress conditions and functions in stress compensation and lignification.

The expression levels of other cDNAs were also found to be two-fold upregulated. These include the cDNAs for jasmonate-induced protein (JAS) and the salt stress-induced protein (SSIP).

Real-Time Quantitative RT-PCR Analysis of Gene Expression in Stem

The expression patterns of four selected cDNAs that were upregulated at least two-fold in the microarray analysis were further assessed by real-time quantitative PCR (RT-PCR). The four cDNAs include OMT, JAS clone 20F18, JAS clone 6H10 and SSIP. The real-time RT-PCR approach allows the identification of false positives obtained through the microarray analysis as well as the differentiation between members of multigene families.

Figure 7:
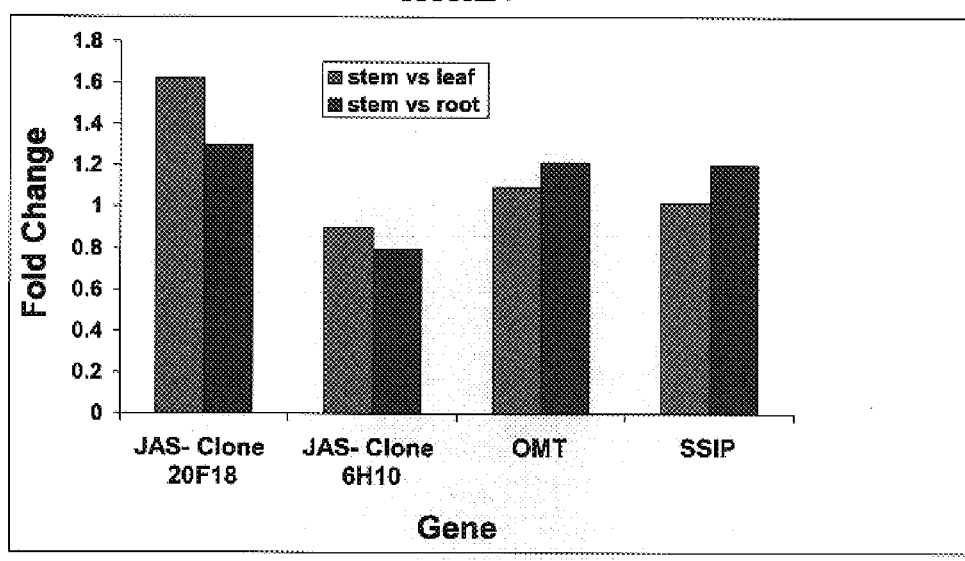
FIG. 7 graphically depicts the fold change in the RNA levels of three stem-regulated cDNAs, OMT, JAS and SSIP in stem vs leaf and stem vs root, as evaluated by real-time quantitative RT-PCR.

Total RNA (2 μg) was extracted from sugarcane stem, leaf or root and the corresponding cDNA templates were generated through RT-PCR using the TaqMan reverse transcription kit (Applied Biosystems). PCR was then performed using the cDNA templates and primers that are specific to the cDNAs of OMT, JAS, SSIP and ubiquitin (endogenous control). Primers were designed by the Primer Express software (Applied Biosystems) and labeled with the fluorescent SYBR Green 1 dye that binds to double-stranded DNA (SYBR Green PCR master mix; Applied Biosystems). The increase in fluorescence was measured for each PCR cycle with the ABI Prism 7700 Sequence Detection System (Applied Biosystems) since the incorporation of SYBR Green 1 dye into a real-time PCR reaction allows the detection of any double-stranded DNA generated during PCR. Real-time RT-PCR quantitations (Ct values) for the four cDNAs as normalized to the endogenous constitutive control ubiquitin are shown in FIG. 7. These results demonstrate that OMT as well as SSIP and the two JAS clones are strongly expressed in stem as compared to leaf or root.

Quantitative RNA Gel Blot Analysis of Gene Expression in Stem

Figure 8:
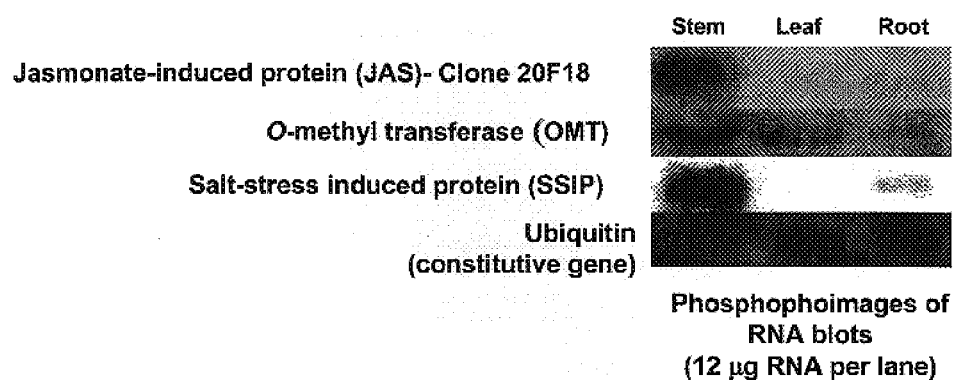
FIG. 8 is an RNA gel blot analysis of the RNA levels of three stem-regulated cDNAs, OMT, JAS and SSIP in sugarcane leaf, stem and root.

To further confirm actual upregulation of OMT in sugarcane stem, a quantitative RNA gel blot analysis was performed using total RNA (12.mu.g) from stem, leaf or root and radioactive probes specific to OMT, SSIP, JAS clone 20F18 and ubiquitin. Hybridization signals were recorded with a Fujix BAS 2000 phosphoimager. The data were analyzed using MacBas software. The hybridization signal for each sample was quantitated and adjusted for loading by virtue of hybridization to a ubiquitin cDNA probe. The quantitative accumulation of OMT, JAS and SSIP was determined and compared to that of the constitutive ubiquitin gene (See FIG. 8). All 3 cDNAs were highly expressed only in stem.

The OMT upregulation as confirmed by the three analytical methods described above is summarized in Table 1.

TABLE 1

Fold Change in OMT expression levels in Different Tissues: Upregulation of OMT in Stem Tissue

| Microarray fold increase | RT-PCR fold change | | RNA gel blot fold change | |
|---|---|---|---|---|
| (stem v. leaf) | Stem v. leaf | Stem v. root | Stem v. leaf | Stem v. root |
| 2.1 | 1.1 | 1.1 | 1.0 | 1.0 |

Example 2

Effects of Defense-Inducing Agents on OMT Upregulation

The 251 cDNA clones used for microarray analysis in Example 1 were further used to assess the effects of defense-inducing agents on the expression of the stem-specific genes.

Total RNA was extracted from wild type sugarcane plants (3 months-old) that were sprayed with the defense-inducing agents jasmonic acid (JA) (25.mu.M in 0.05.percent.Tween 20), methyl-jasmonate (MeJA) (200.mu.M in 0.1.percent.ethanol and 0.05.percent.Tween 20) or salicylic acid (SA) (5 mM in 0.05.percent.Tween 20) for two time periods, 24 and 48 hours. The microarray including 251 cDNAs was probed with fluorescently labeled cDNAs synthesized from 1.mu.g of total amplified RNA. One cDNA probe (e.g. RNA from plant treated with a defense-inducing agent) is labeled with one dye (Cy5), and the second (e.g. RNA from untreated control plant) with another dye (Cy3)

The normalized ratio of Cy5 v. Cy3 for OMT intensity after treatment with each defense-inducing agent is summarized in Table 2.

TABLE 2

Cy5/Cy3 Ratios (Upregulation) for OMT
Following Treatment with Defense-Inducing Agents

| JA Treatment | | MeJA Treatment | | SA treatment |
|---|---|---|---|---|
| 24 hours | 48 hours | 24 hours | 48 hours | 48 hours |
| 0.99 | 2.00 | 0.70 | 0.97 | 2.00 |

These results show that the OMT gene is upregulated by approximately 48 hours after treatment with a defense-inducing agent.

Example 3

Isolation and Cloning of Genomic Sequence Corresponding to OMT Gene and Promoter Release Initially, an attempt was made to use PCR walking to clone the OMT promoter directly from genomic DNA. However, the complexity of the sugarcane genome and the presence of substantial amounts of repetitive DNA in it rendered this approach unworkable.

A second attempt to locate the OMT promoter was made using a sugarcane bacteriophage lambda genomic library. 23 replica filters were probed using a full-length OMT cDNA probe. Three screening were performed to select genomic clones exhibiting strong hybridization to OMT cDNA. Phage DNA was isolated from 10 candidate OMT genomic clones and digested with restriction endonucleases (EcoRI, HindIII, NotI and XbaI) prior to DNA gel blot analysis. DNA gel blot analysis (shown in FIG. 9) revealed several unique restriction fragments containing the OMT gene. This indicated that the 10 OMT clones were most likely members of a multigene family.

Two clones (Clones 14 and 15) were selected for further study. A 4.3 kb XbaI fragment of Clone 14 (OMT1) was subcloned into the polylinker site of the pBluescript sequencing vector (Strategene) and sequenced by cycle sequencing using an ABI PRISM dye terminator cycle sequencing kit. The 6.2 kb XbaI fragment of Clone 15 (OMT2) was similarly treated. These identities of these clones as OMT clones was thus verified.

A 3.0 kb promoter fragment was released from the 4.2 kb OMT1 genomic clone. (See SEQ ID NO: 1.) This promoter fragment is shown in FIG. 1. A 5.0 kb promoter was released from the 6.2 kb OMT2 clone.

Example 4

Vector Construction and Expression In Planta

Two sugarcane expression vectors were produced by cloning either the OMT1 promoter or the OMT2 promoter into a pUC19 GUS reporter vector to produce pOMT1::GUSpUC19 and pOMT2::GUSpUC19 vectors. (See FIG. 2.) Specifically, the 35S promoter normally found in pUC19 GUS was replaced with an OMT promoter at the corresponding XbaI and NcoI restriction sites to create a translational fusion with the GUS reporter DNA.

A rice expression vector was also produced by cloning the pOMT1 promoter into the plant binary expression vector pCambia 1301 to create pOMT::GUSpCambia. (See FIG. 3.) The 35S promoter normally pCambia 1301 was replaced at the corresponding XbaI and NcoI restriction sites to create a translational fusion with the GUS reporter DNA.

Stable expression of GUS under control of the OMT promoter was achieved in sugarcane. Furthermore, such expression was stem-specific.

Figure 10:
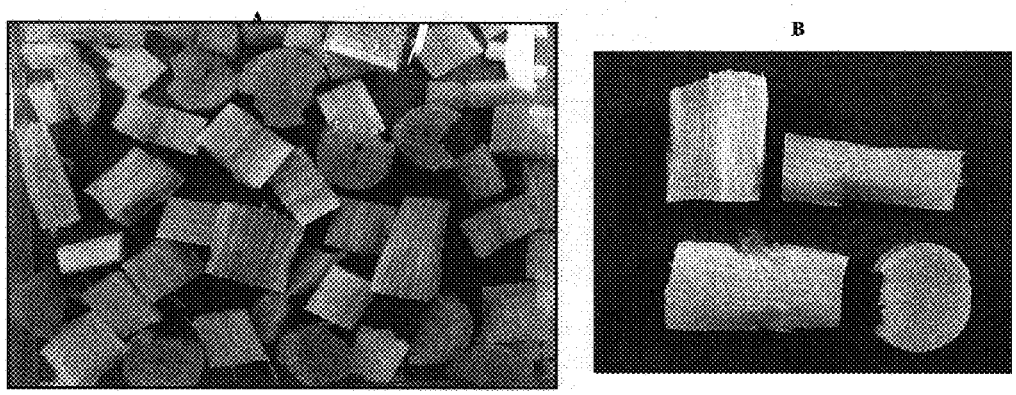
FIG. 10A is a photomicrograph of transgenic sugarcane stems showing histochemical localization of GUS gene expression driven by the stem-regulated OMT promoter.
FIG. 10B is a close-up photo showing GUS expression in the stem nodal area and vascular tissue.

Specifically, embryonic calli of sugarcane cultivar CP72-1210 were transformed with pOMT::GUSpUC vectors using gene gun/biolistic-mediated transfer (Irvine and Mirkov, 1997 Sugar Journal 60:25-29; Inglebrecht et al, 1999 Plant Physiol. 119;1187-1197). Histochemical localization of GUS expression was determined using 5-bromo-4-chloro-3-indoyl glucuronide. (See FIG. 10A.) Intense GUS staining was observed in the stem nodal area and vascular bundles. (See FIG. 10B.)

Figure 11:
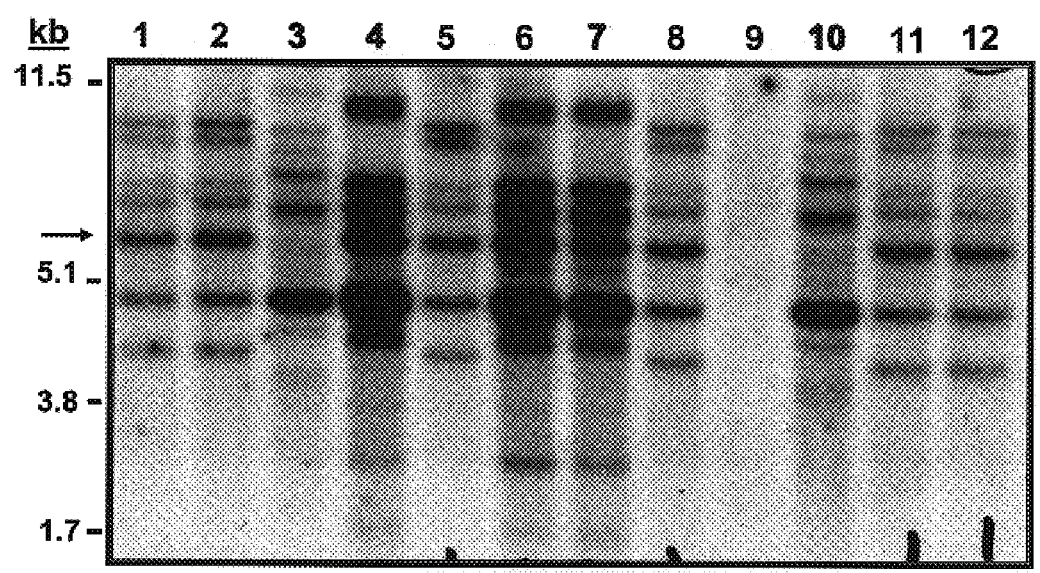
FIG. 11 is a genomic DNA gel blot analysis of HindIII digested sugarcane genomic DNA hybridized with GUS gene probe. Lanes 1, 2, 5, 8, 11 & 12: One positive transformation event; Lanes 4, 6 & 7: Another positive event; Lanes 3 & 10: A negative event.

The generated sugarcane OMT transgenic lines were analyzed by DNA gel blot. HindIII digested genomic DNA from the transgenic lines were hybridized with a GUS probe. Results showed the presence of at least one copy of the GUS transgene in most lines analyzed. Several lines had multiple copies. (See FIG. 11.)

Figure 12:
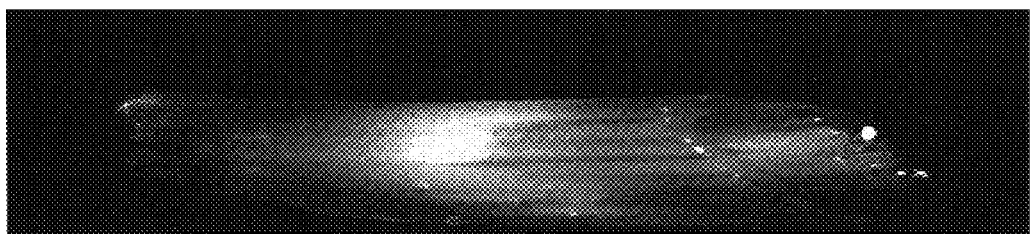
FIG. 12 is a photomicrograph of transgenic rice stems showing histochemical localization of GUS expression driven by the stem-regulated OMT promoter.
Figure 13:
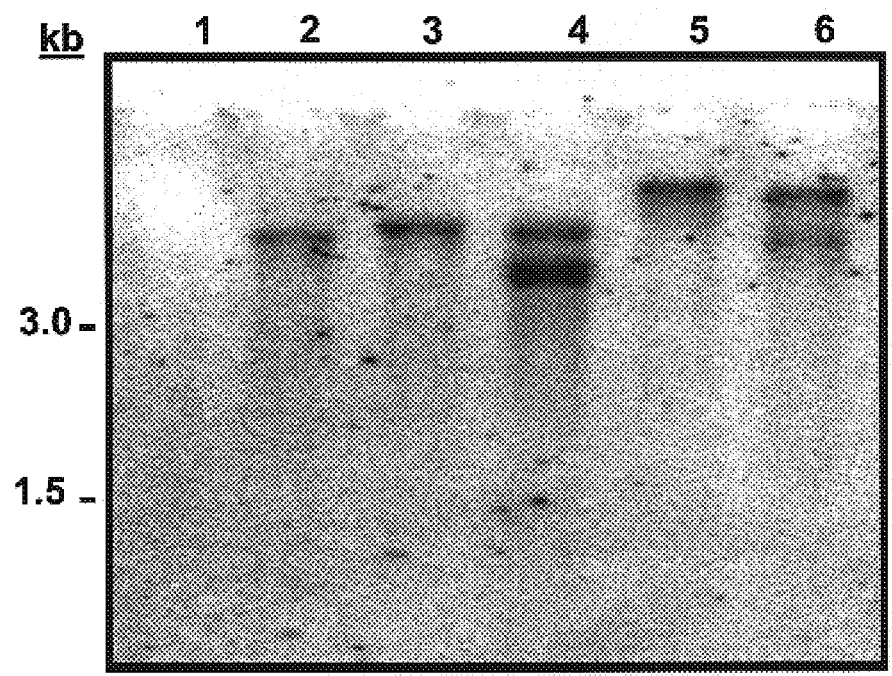
FIG. 13 is a phosphoimage of DNA gel blot analysis of HindIII digested rice genomic DNA hybridized to hygromycin gene probe. Lane 1: Untransformed plant; Lanes 2, 3, 4 & 5: 3 independent pOMT1::GUS lines; Lane 6: one pOMT2::GUS line.

Embryonic rice calli (Taipei 309) were transformed with pOMT:pUCpCambia using *Agrobacterium tumefaciens* EHA 105 (Aldemita and Hodges 1996). 27 lines for each of pOMT1 and pOMT2 were created. Histochemical analysis of transformed clones showed intense GUS staining in the stem vascular bundles. (See FIG. 12.) HindIII digested genomic DNA from the transgenic lines were hybridized with a hygromycin probe. Results showed the presence of at least one copy of the hygromycin transgene in most lines analyzed. (See FIG. 13.)

Analysis of GUS expression in pooled tissue was used to confirm the presence of GUS in transformed plants. Expression as compared to that driven by maize ubiquitin 1 was also studied. The results of this analysis are presented in Table 3.

TABLE 3

Evaluation of GUS Activity in Transgenic Rice
under control of OMT Promoter or Ubiquitin Promoter

| Line | | Tissue (pooled tissues of 3 tillers/plant) | | |
|---|---|---|---|---|
| | | Stem | Leaf | Root |
| Untransformed | | 0.19 ± 0.01 | 0.1 ± 0.0001 | 0.44 ± 0.11 |
| pOMT1::GUS | #24 | 17.22 ± 26.92 | 4.89 ± 0.12 | 2.13 ± 0.13 |
| | #42 | 871.92 ± 57.19 | 23.12 ± 6.84 | 36.48 ± 3.60 |
| | #53 | 1465.56 ± 183.00 | 76.75 ± 17.65 | 58.65 ± 19.91 |
| pOMT2::GUS | #12 | 15.33 ± 1.74 | 0.37 ± 0.01 | 3.97 ± 1.28 |
| | #18 | 48.13 ± 5.07 | 0.48 ± 0.04 | 0.24 ± 0.02 |

TABLE 3-continued

Evaluation of GUS Activity in Transgenic Rice
under control of OMT Promoter or Ubiquitin Promoter

|  |  | Tissue (pooled tissues of 3 tillers/plant) | | |
| --- | --- | --- | --- | --- |
| Line |  | Stem | Leaf | Root |
| pUbi1::GUS | #5 | 32.59 ± 1.38 | 1.51 ± 0.21 | 7.22 ± 0.28 |
|  | #12 | 181.12 ± 30.40 | 1043.88 ± 142.25 | 1641.76 ± 98.16 |
|  | #13 | 1418.22 ± 409.17 | 337.25 ± 88.43 | 158.60 ± 10.43 |

Values expressed are pmole 4-methylumbelliferyl -D- glucuronide/.micro. total protein/minute. All assays were performed in triplicate on 2 separate batches of samples.

Similar histochemical analysis also showed transient expression of GUS under the OMT promoter in stem tissues of sorghum and maize at a level comparable to that obtained with the Ubiquitin 1 promoter. (See FIG. 14.)

After stem-specific expression of GUS under an OMT promoter was confirmed, a transgenic rice line (#42) that showed high levels of pOMT-driven expression was tested for segregation of the transgene during reproduction. 40 seeds of the T0 generation were planted. The T1 generation was tested for localization of GUS expression. 3.4:1 plants of the T1 generation expressed GUS in the stem. This indicates Mendelian inheritance of the transgene.

The invention claimed is:

1. An isolated nucleic acid comprising a promoter having the sequence of SEQ ID NO: 1, wherein the promoter has stem-regulated promoter activity.

2. The nucleic acid of claim 1 further comprising an exogenous nucleic acid, wherein the promoter is operable to drive stem-regulated expression or transcription of the exogenous nucleic acid.

3. The nucleic acid of claim 2, wherein the promoter is further operable to drive upregulated stem-regulated expression or transcription in the presence of a defense-inducing agent.

4. An expression vector comprising, in a 5' to 3' direction:
a promoter having the sequence of SEQ ID NO: 1;
an exogenous nucleic acid; and
a 3' termination sequence.

5. The expression vector of claim 4, wherein the exogenous nucleic acid comprises a transgene.

6. A monocot plant cell comprising an expression vector having:
the promoter having a sequence of SEQ ID NO: 1 and operable in the monocot plant cell;
an exogenous nucleic acid; and
a 3' termination sequence.

7. The plant cell of claim 6, wherein the exogenous nucleic acid comprises a transgene.

8. The plant cell of claim 6, wherein the exogenous nucleic acid alters carbon metabolism in the plant cell when expressed or transcribed.

9. The plant cell of claim 6, wherein the exogenous nucleic acid encodes an insecticide effective against at least one stem-boring insect.

10. A monocot plant comprising an expression vector having:
a promoter having the sequence of SEQ ID NO: 1 and operable in the monocot plant;
an exogenous nucleic acid; and
a 3' termination sequence,
wherein expression of the exogenous nucleic acid is stem-regulated.

11. The plant of claim 10, wherein expression of the exogenous nucleic acid is upregulated by the presence of a defense-inducing agent.

12. The plant of claim 10, wherein the exogenous nucleic acid alters carbon metabolism in at least one plant cell of the plant when expressed or transcribed.

13. The plant of claim 10, wherein the exogenous nucleic acid encodes an insecticide effective against at least one stem-boring insect.

14. The plant of claim 10, wherein the plant is selected from the group consisting of: sugarcane, sorghum, rice, maize and any hybrids thereof.

15. A bacterial cell comprising an expression vector having:
a promoter having the sequence of SEQ ID NO: 1;
an exogenous nucleic acid; and
a 3' termination sequence.

16. A method of directing stem-regulated expression of a nucleic acid in a monocot plant comprising:
providing an expression nucleic acid having a promoter having the sequence of SEQ ID NO: 1, an exogenous nucleic acid and a 3' termination sequence; and
transforming the monocot plant with the expression nucleic acid;
wherein expression of the exogenous nucleic acid is stem-regulated.

17. The method of claim 16, further comprising providing an expression vector comprising the promoter having the sequence of SEQ ID NO:1, an exogenous nucleic acid and a 3' termination sequence.

18. The method of claim 16, wherein transforming further comprises gene gun/biolistic-mediated transformation.

19. The method of claim 16, wherein transforming further comprises *Agrobacterium*-mediated transformation.

20. The method of claim 16, further comprising transforming an embryonic callus.

21. The method of claim 20, further comprising regenerating a plant from the embryonic callus.

22. The method of claim 16, further comprising transforming a plant cell.

23. The method of claim 16, further comprising breeding progeny of the transformed plant.

24. A method of directing stem-regulated expression of a nucleic acid in a monocot plant comprising:
providing an expression nucleic acid having a promoter having the sequence of SEQ ID NO: 1, an exogenous nucleic acid and a 3' termination sequence; and
transforming the monocot plant with the expression nucleic acid;
wherein expression of the exogenous nucleic acid is induced by a defense-inducing agent.

25. The method of claim 24, further comprising providing an expression vector comprising the promoter having the sequence of SEQ ID NO:1, an exogenous nucleic acid and a 3' termination sequence.

26. The method of claim 24, wherein transforming further comprises gene gun/biolistic-mediated transformation.

27. The method of claim 24, wherein transforming further comprises *Agrobacterium*-mediated transformation.

28. The method of claim 24, further comprising transforming an embryonic callus.

29. The method of claim 28, further comprising regenerating a plant from the embryonic callus.

30. The method of claim 24, further comprising transforming a plant cell.

31. The method of claim 24, further comprising breeding progeny of the transformed plant.

32. The plant cell of claim 6, wherein the plant cell is from a plant selected from the group consisting of: sugarcane, sorghum, rice, maize and any hybrids thereof.

* * * * *

SEQUENCE LISTING

```
<160> NUMBER OF SEQ ID NOS: 1

<210> SEQ ID NO 1
<211> LENGTH: 3016
<212> TYPE: DNA
<213> ORGANISM: Sugarcane
<220> FEATURE:
<221> NAME/KEY: promoter
<222> LOCATION: (1)...(3012)
<223> OTHER INFORMATION: o-methyltransferase promoter
<220> FEATURE:
<221> NAME/KEY: CAAT_signal
<222> LOCATION: (2661)...(2664)
<220> FEATURE:
<221> NAME/KEY: TATA_signal
<222> LOCATION: (2849)...(2855)

<400> SEQUENCE: 1
tctagagcat aggcattgta aaagcggtat gcctcttctt cagtgcagaa tttcatacca      60
accttaggta tcctgtcttc catagaattt tctacctgag taggttcggt ctggttggat     120
ttgtagcggg tttcatgcaa aataagttag aaatcgtgca aacttgcaat ggaggttaaa     180
tttgaaatat atttgcatag acaaaacaaa tatagattat gaatggtaat ccaatatgac     240
ttgcattttc taactctatt gctactgtgc cagatgaaga atgttgatct ggagaagttt     300
tgtgagaatg tgacaacaac gggaggtcat atcaagattc tgggtacccg cggagaatcg     360
gcctccatgt agttagcctc gtcaggcatg gggggaattg gctgagatgc ccccatgtag     420
tcgtcaggca tggagagtac tggctgagat gccattgttg tgtagatcga gagaaacgag     480
aagaatgcta gtctaataat acccttccgt atgctaacca actattataa ttggcaccat     540
ttttcacatg ctagcgcctt ttgcctgctt tatttaattc aattgggtcc gataagcatg     600
tgaacgtggg agacggttcc gtcggacggc tccgttttct tgtagcgtac ggcgtggacg     660
gagaaaaggt gagggcctat ctctaaaggg gaacgaatgg atggtggaca cgtgtgggga     720
gacaccgaag ggacatgccg aggaggcaca caagcttcag caggcgtctc cagactctca     780
gaagaagaag aagctcacgg cacggttgcg gctggttctt gctgtcgctg tctcgtggtg     840
cacgtttctg tgatcacgct gaaatcgacc ggccggcgga ccaacaggag gtcagctcgg     900
```

```
ccactccgtc tccgagcgca tgagtgcacc gttcgtccgc ggttccttt tctcgtggtgc    960
cgtgcacgcc tctgcgttca ccggcaccct gaaaccaatc agaacgttcc ctttacaggg   1020
gaaagggaca agtctgataa cctctctgtt tccatcgtcc tctaaccgcg aagagcggac   1080
gcacaagact tagagtctat ttgttcgaaa tttttactc tcacaaaagc tagcttttat    1140
agacgggcat aaaagctatc atgtcgaccg gcacgtttaa tatttaactt ataccatatg   1200
aatatcatgt cgaactatga ggatgatact tttctgaacg tgattgcgtg agttattaaa   1260
ttgtactttt agttgtttga gcatgaaggt ctgaactatg aatttatgat gtattgtggc   1320
ttgtgagcta ctccgctcta catttagttg gtatcataaa tattattata ttatcatata   1380
aatttgatca acttgagatg ctttgactct tcaagattct tggaatgact tatcatttgg   1440
ggtagggagt aggtttctaa ggccagtctc agtggggttt catcagagtt tcatggacat   1500
taaataagct gatgtgacac cgtattgatg aagagagaga tgataagagt ttcatgcgag   1560
tagagagagt ttcatgggga tgaaactctt cttcactgtt tccaaaatat agatgcattg   1620
gtaagagggc catgaaatct ctagtgacac tgacctaaga tgagattgac tctagcacta   1680
tgtttcaaaa tctgcatgca tgcatgcttt gaatattgta acctcacatt aactcccctc   1740
acacatgcat gcaaacgggc ggtgcacgca aagaattga gtgaagatgc acatgaaaaa    1800
taagtaaaat gctttggctt catcacccgg cttaaatgct cgacagaaaa acacgtcggt   1860
agtcaaggtt gtgcctaaca aactggggtt cacatgtaaa acacgttcat gccttagaaa   1920
cggcctggag ggattagata caacttcaat tatatcttag ggcccctcca atattgtcag   1980
ctctaaacta gttttatgtg tcacggtgga ggagagggag gctaaaaata taatcttgag   2040
ctaacgtgaa gagaagagct attttttttt gctccccaat acatgataga tacaatatga   2100
gagaaaaaat atatgaataa agaacacttt acatgccagc catacaatat gagatttcat   2160
ctaagagcca acacctgact cgtactgttg aaggtgtcct agttggagtg gtcgatcttt   2220
tagttgttag tagtgtaaga cctagtttag tgctcttttc ttgtctaggt ttatgttgtg   2280
ttttggctgc caagtgttga acaactcaag gtaaggtccc atctaattct aaaatgatgc   2340
caaataaaga tagattacaa agttaaacga cggaaaaact ctaaaatagg atggaaagtt   2400
ttgtagagta ataattggta tgaagtggcg aagtcgacca caaccaaaca taagagtta    2460
aatgcatggt aggctcttga tcttgtctgg aggtgccact taggtccaca aactctcaaa   2520
ttgcattttt gacaccctaa tgttattcaa gtgtgccact tagatctaca aactctcaaa   2580
atgcatttct gataccctag tgttgttcaa gtgtgtcact taggcaagaa aagttagata   2640
attttgataa gctatgggac caaattaatt tatgtatgca tgctcgaact agttgatgat   2700
gatggacccc ataatagaca ctagttcatg ggctggtttc cttgtatagt actagctagt   2760
ataacttttt caagttgtag ctactacttt agcttatact ccgcatatta caatcaaata   2820
gaattcggaa gtactataaa cgggagccta taaatggaga cgttttgcat catgaggcta   2880
taacaacttg agcaaaaaca gaagccgtgc gccatggcgc tcagcaagga gcaacacaca   2940
agcactgatc agcaggccgt gctggatgct cagctccagc tctggcacca caccctgggc   3000
tatgtcaagt ccatgg                                                   3016
```